US007547545B2

(12) United States Patent
Prockop et al.

(10) Patent No.: US 7,547,545 B2
(45) Date of Patent: Jun. 16, 2009

(54) DIRECTED IN VITRO DIFFERENTIATION OF MARROW STROMAL CELLS INTO NEURAL CELL PROGENITORS

(76) Inventors: Darwin J. Prockop, 1750 St. Charles Ave., Apt. 522, New Orleans, LA (US) 70130; Weiwen Deng, 3443 Edenborn Ave., Apt. 312, Metairie, LA (US) 70002

( * ) Notice: Subject to any disclaimer, the term of this patent is extended or adjusted under 35 U.S.C. 154(b) by 177 days.

(21) Appl. No.: 11/484,670

(22) Filed: Jul. 12, 2006

(65) Prior Publication Data
US 2007/0036772 A1    Feb. 15, 2007

Related U.S. Application Data

(62) Division of application No. 10/153,972, filed on May 23, 2002, now abandoned.

(60) Provisional application No. 60/294,281, filed on May 30, 2001.

(51) Int. Cl.
*C12N 15/00* (2006.01)
*C12N 15/04* (2006.01)

(52) U.S. Cl. .................. 435/373; 435/325; 435/366

(58) Field of Classification Search .................. None
See application file for complete search history.

(56) References Cited

FOREIGN PATENT DOCUMENTS

| WO | WO 96-30031 | 10/1996 |
|----|----|----|
| WO | WO 99-43286 | 9/1999 |

OTHER PUBLICATIONS

Hicok et al. Development and Characterization of Conditionally Immortalized Osteoblast Precursor Cell Lines from Human Bone Marrow Stroma. Journal of Bone and Mineral Res. 1998, vol. 13, No. 2, pp. 205-217.*
Austin et al. "A Role for the Wnt Gene Family in Hematopoiesis: Expansion of Multilineage Progenitor Cells", Blood, vol. 89, No. 10, 1997, pp. 3624-3635.
Azizi et al. "Engraftment and migration of human bone marrow stromal cells implanted in the brains of albino rats—similarities to astrocyte grafts", PNAS, vol. 95, 1998, pp. 3908-3913.
Bang et al. "Terminal neuroendocrine differentiation of human prostate carcinoma cells in response to increased intracellular cyclic AMP", PNAS, vol. 91, 1994, pp. 5330-5334.
Beresford et al. "Evidence for an inverse relationship between the differentiation of adipocytic and osteogenic cells in rat marrow stromal cell cultures", Journal of Cell Science, 102, 1992, pp. 341-351.
Bjornson et al. "Turning Brain into Blood: A Hematopoietic Fate Adopted by Adult Neural Stem Cells in Vivo", Science, vol. 283, 1999, pp. 534-537.
Blackburn. "Switching and Signaling at the Telomere", Cell, vol. 106, 2001, pp. 661-673.
Brundin et al. "Bilateral caudate and putamen grafts of embryonic mesencephalic tissue treated with lazaroids in Parkinson's disease", Brain, vol. 123, 2000, pp. 1380-1390.

Cao et al. "Stem Cell Repair of Central Nervous System Injury", Journal of Neuroscience Research, vol. 68, 2002, pp. 501-510.
Caplan. "Mesenchymal Stem Cells and Gene Therapy", Clinical Orthopaedics and Related Research, No. 379S, 2000, pp. S67-S70.
Castro-Malaspina et al. "Characterization of Human Bone Marrow Fibroblast Colony—Forming Cells (CFU-F) and Their Progeny", Blood, vol. 56, No. 2, 1980, pp. 289-301.
Chopp et al. "Spinal cord injury in rat: treatment with bone marrow stromal cell transplantation", NeuroReport, vol. 11, No. 13, 2000, pp. 3001-3005.
Clark et al. "Biology of Bone Marrow Stroma", Annals New York Academy of Science, pp. 70-78.
Colter et al. "Identification of a subpopulation of rapidly self renewing and multipotential adult stem cells in colonies of human marrow stromal cells", PNAS, vol. 98, No. 14, 2001, pp. 7841-7845.
Colter et al. "Rapid expansion of recycling stem cells in cultures of plastic-adherent cells from human bone marrow", PNAS, vol. 97, No. 7, 2000, pp. 3213-3218.
Cox et al. "Acquisition of Neuroendocrine Characteristics by Prostate Tumor Cells Is Reversible: Implications for Prostate Cancer Progression", Cancer Research, vol. 59, 1999, pp. 3821-3830.
De Cristobal et al. "Neuroprotective effect of aspirin by inhibition of glutamate release after permanent focal cerebral ischaemia in rats", Journal of Neurochemistry, vol. 79, 2001, pp. 456-459.
Deng et al. "In Vitro Differentiation of Human Marrow Stromal Cells into Early Progenitors of Neural Cells by Conditions That Increase Intracellular Cyclic AMP", Biochemical and Biophysical Research Communications, vol. 282, 2001, pp. 148-152.
DiGirolamo et al. "Propagation and senescence of human marrow stromal cells in culture: a simple colony-forming assay identifies samples with the greatest potential to propagate and differentiate", British Journal of Haematology, vol. 107, 1999 pp. 275-281.
Dumont et al. "Acute Spinal Cord Injury, Part II: Contemporary Pharmacotherapy", Clinical Neuropharmacology, vol. 24, No. 5, 2001, pp. 265-279.
Ferrari et al. "Muscle Regeneration by Bone Marrow-Derived Myogenic Progenitors", Science, vol. 279, 1998, pp. 1528-1530.
Flax et al. "Engraftable human neural stem cells respond to developmental cues, replace neurons, and express foreign genes", Nature Biotechnology, vol. 16, 1998, pp. 1033-1039.

(Continued)

*Primary Examiner*—Deborah Crouch
(74) *Attorney, Agent, or Firm*—Benjamin Aaron Adler

(57) ABSTRACT

The invention relates to methods for inducing marrow stromal cells to differentiate into neural cells by way of increasing intracellular levels of cyclic AMP. The invention also encompasses methods of producing a neural cell by causing a marrow stromal cell to differentiate into a neural cell by increasing intracellular levels of cyclic AMP. Methods for treating a human patient in need of neural cells are also disclosed, as well as methods for treating a human patient having a disease, condition, or disorder of the central nervous system.

18 Claims, 3 Drawing Sheets

OTHER PUBLICATIONS

Friedenstein et al. "The Development of Fibroblast Colonies in Monolayer Cultures of Guinea-Pig Bone Marrow and Spleen Cells", Cell Tissue Kinet, vol. 3, 1970, pp. 393-403.

Gage et al. "Isolation, Characterization, and use of Stem Cells from the CNS", Annu. Rev. Neurosci, vol. 18, 1995, pp. 159-192.

Ghosh et al. "Intercellular Communication in Rapidly Proliferating and Differentiated C6 Glioma Cells in Culture", Cell Biology International vol. 21, No. 9, 1997, pp. 551-557.

Gregory et al. "Dkk-1-derived Synthetic Peptides and Lithium Chloride for the Control and Recovery of Adult Stem Cells from Bone Marrow", The Journal of Biological Chemistry, vol. 280, No. 3, 2005, pp. 2309-2323.

Gregory et al. "Quantification of *Escherichia coli* Genomic DNA Contamination in Recombinant Protein Preparations by Polymerase Chain Reaction and Affinity-Based Collection", Analytical Biochemistry, vol. 296, 2001, pp. 114-121.

Hagell et al. "Dyskinesias following neural transplantation in Parkinson's disease", Nature Neuroscience, vol. 5, No. 7, 2002, pp. 627-628.

Hofstetter et al. "Marrow stromal cells form guiding strands in the injured spinal cord and promote recovery", PNAS, vol. 99, No. 4, 2002, pp. 2199-2204.

Horwitz et al. "Transplantability and therapeutic effects of bone marrow-derived mesenchymal cells in children with osteogenesis imperfecta", Nature Medicine, vol. 5, No. 3, 1999, pp. 309-313.

Iwata et al. "Interleukin-1 (IL-1) Inhibits Growth of Cytomegalovirus in Human Marrow Stromal Cells: Inhibition Is Reversed Upon Removal of IL-1", Blood, vol. 94, No. 2, 1999, pp. 572-578.

Jiang et al. "Pluripotency of mesenchymal stem cells derived from adult marrow", Nature, vol. 418, 2002, pp. 41-49.

Johansson et al. "Identification of a Neural Stem Cell in the Adult Mammalian Central Nervous System", Cell, vol. 96, 1999, pp. 25-34.

Ko et al. "Biochemical and functional characterization of intercellular adhesion and gap junctions in fibroblasts", Am J Physiol Cell Physiol, vol. 279, 2000, pp. C147-C157.

Kopen et al. "Marrow stromal cells migrate throughout forebrain and cerebellum, and they differentiate into astrocytes after injection into neonatal mouse brains", PNAS, vol. 96, 1999, pp. 10711-10716.

Kotton et al. "Bone marrow-derived cells as progenitors of lung alveolar epithelium", Development, vol. 128, 2001, pp. 5181-5188.

Krause et al. "Multi-Organ, Multi-Lineage Engraftment by a Single Bone Marrow-Derived Stem Cell", Cell, vol. 105, 2001, pp. 369-377.

Labombarda et al. "Cellular Basis for Progesterone Neuroprotection in the Injured Spinal Cord", Journal of Neurotrauma, vol. 19, No. 3, 2002, pp. 343-355.

Lennon et al. "A Chemically Defined Medium Supports in Vitro Proliferation and Maintains the Osteochondral Potential of Rat Marrow-Derived Mesenchymal Stem Cells", Experimental Cell Research, vol. 219, 1995, pp. 211-222.

Liechty et al. "Human mesenchymal stem cells engraft and demonstrate site-specific differentiation after in utero transplantation in sheep", Nature Medicine, vol. 6, No. 11, 2000, pp. 1282-1286.

Lundberg et al. "Conditionally immortalized neural progenitor cell lines integrate and differentiate after grafting to the adult rat striatum. A combined Autoradiographic and electron microscopic study", Brain Research, vol. 737, 1996, pp. 295-300.

Lundberg et al. "Survival, Integration, and Differentiation of Neural Stem Cell Lines after Transplantation to the Adult Rat Striatum", Experimental Neurology, vol. 145, 1997, pp. 342-360.

Mazzini et al. "Stem cell therapy in amyotrophic lateral sclerosis: a methodological approach in humans", ALS and Other Motor Neuron Disorders, vol. 4, 2003, pp. 158-161.

Morshead et al. "Neural Stem Cells in the Adult Mammalian Forebrain: A Relatively Quiescent Subpopulation of Subependymal Cells", Neuron, vol. 13, 1994, pp. 1071-1082.

Nelson et al. "Convergence of Wnt, B-Catenin, and Cadherin Pathways", Science, vol. 303, 2004, pp. 1483-1487.

Oka et al. "Autologous transplantation of expanded neural precursor cells into the demyelinated monkey spinal cord", Brain Research, vol. 1030, 2004, pp. 94-102.

Okamoto et al. "Damaged epithelia regenerated by bone marrow-derived cells in the human gastrointestinal tract", Nature Medicine, vol. 8, No. 9, 2002, pp. 1011-1017.

Park et al. "Global gene and cell replacement strategies via stem cells", Gene Therapy, vol. 9, 2002, pp. 613-624.

Pesce et al. "Oct-4: Gatekeeper in the Beginnings of Mammalian Development", Stem Cells, vol. 19, 2001, pp. 271-278.

Petersen et al. "Bone Marrow as a Potential Source of Hepatic Oval Cells", Science, vol. 284, 1999, pp. 1168-1170.

Pittenger et al. "Multilineage Potential of Adult Human Mesenchymal Stem Cells", Science, vol. 284, 1999, pp. 143-147.

Prockop et al. "One strategy for cell and gene therapy: Harnessing the power of adults stem cells to repair tissues", PNAS, vol. 100, Suppl. 1, 2003, pp. 11917-11923.

Prockop. "Marrow Stromal Cells as Stem Cells for Nonhematopoietic Tissues", Science, vol. 276, 1997, pp. 71-74.

Renfranz et al. "Region-Specific Differentiation of the Hippocampal Stem Cell Line HiB5 upon Implantation into the Developing Mammalian Brain", Cell, vol. 66, 1991, pp. 713-729.

Reynolds et al. "Generation of Neurons and Astrocytes from Isolated Cells of the Adult Mammalian Central Nervous System", Science, vol. 255, No. 5052, 1992, pp. 1707-1710.

Rezkalla et al. "Antiplatelet Therapy from Clinical Trials to Clinical Practice", Clinical Medicine & Research, vol. 1, No. 2, 2003, pp. 101-104.

Richards et al. "De novo generation of neuronal cells from adult mouse brain", PNAS, vol. 89, 1992, pp. 8591-8595.

Rossi et al. "Neural stem cell therapy for neurological diseases: dreams and reality", Neuroscience, vol. 3, 2002, pp. 401-409.

Rost et al. "Protein Fold Recognition by Prediction-based Threading", Mol. Biol., vol. 270, 1997, 471-480.

Sanchez-Ramos et al. "Adult Bone Marrow Stromal Cells Differentiate into Neural Cells in Vitro", Experimental Neurology, vol. 164, 2000, pp. 247-256.

Sanchez-Ramos. "Neural Cells Derived From Adult Bone Marrow and Umbilical Cord Blood", Journal of Neuroscience Research, vol. 69, 2002, pp. 880-893.

Schwarz et al. "Multipotential Marrow Stromal Cells Transduced to Produce L-DOPA: Engraftment in a Rat Model of Parkinson Disease", Human Gene Therapy, vol. 10, 1999, pp. 2539-2549.

Sekiya et al. "In vitro cartilage formation by human adult stem cells from bone marrow stroma defines the sequence of cellular and molecular events during chondrogenesis", PNAS, vol. 99, No. 7, 2002, pp. 4397-4402.

Sharma et al. "Transient Increase in Intracellular Concentration of Adenosine 3' :5'—Cyclic Monophosphate Results in Morphological and Biochemical Differentiation of C6 Glioma Cells in Culture", Journal of Neuroscience Research, vol. 17, 1987, pp. 135-141.

Spees et al. "Thermal acclimation and stress in the American lobster, *Homarus americanus*: equivalent temperature shifts elicit unique gene expression patterns for molecular chaperones and polyubiquitin", Cell Stress & Chaperones, vol. 7, No. 1, 2002, pp. 97-106.

Svendsen et al. "Long-Term Survival of Human Central Nervous System Progenitor Cells Transplanted into a Rat Model of Parkinson's Disease", Experimental Neurology, vol. 148, 1997, pp. 135-146.

Tao et al. "Evidence for transdifferentiation of human bone marrow-derived stem cells: recent progress and controversies", Pathology, vol. 35, 2003, pp. 6-13.

Terada et al. "Bone marrow cells adopt the phenotype of other cells by spontaneous cell fusion", Nature, vol. 416, 2002, pp. 542-545.

Tian et al. "The Role of Wnt-Signaling Antagonist DKK1 in the Development of Osteolytic Lesions in Multiple Myeloma", N. Engl. J. Med., vol. 349, No. 26, 2003, pp. 2483-3494.

Toma et al. "Human Mesenchymal Stem Cells Differentiate to a Cardiomyocyte Phenotype in the Adult Murine Heart", Circulation, vol. 1, No. 8, 2002, pp. 93-98.

Vescovi et al. "bFGF Regulates the Proliferative Fate of Unipotent (Neuronal) and Bipotent (Neuronal/Astroglial) EGF-Generated CNS Progenitor Cells", Neuron, vol. 11, 1993, pp. 951-966.

Wagers et al. "Cell fate determination from stem cells", Gene Therapy, vol. 9, 2002, pp. 606-612.

Wakitani et al. "Myogenic Cells Derived from Rat Bone Marrow Mesenchymal Stem Cells Exposed to 5-Azacytidine", Muscle & Nerve, vol. 18 1995, pp. 1417-1426.

Wilkins et al. "Cross-Species Protein Identification using Amino Acid Composition, Peptide Mass Fingerprinting, Isoelectric Point and Molecular Mass: A Theoretical Evaluation", J. theor. Biol., vol. 186, 1997, pp. 7-15.

Woodbury et al. "Adult Rat and Human Bone Marrow Stromal Cells Differentiate Into Neurons", Journal of Neuroscience Research, vol. 61, 2000, pp. 364-370.

Ying et al. "Changing potency by spontaneous fusion", Nature, vol. 416, 2002, pp. 545-548.

Bossolasco, P., et al. "Neuro-glial differentiation of human bone marrow stem cells into vitro" *Exp. Neurol.* 193(2):273-278 (Jun. 2005) (abstract only).

Guo, L., et al. "Differentiation of Mesenchymal Stem Cells Into Dopaminergic Neuron-like Cells in vitro" *Biomedical and Environmental Sciences* 18:36-42 (2005).

Hermann, A., et al. "Comparative analysis of neuroectodermal differentiation capacity of human bone marrow stromal cells using various conversion protocols" *J. Neurosci. Res.* 83(8):1502-1514 (Jun. 2006) (abstract only).

Kamishina, H., et al. "Expression of neural markers on bone marrow-derived canine mesenchymal stems cells" *Am. J. Vet. Res.* 67(11):1921-1928 (2006) (abstract only).

Raedt, R., et al. "Differentiation assays on bone marrow-derived Multipotent Adult Progenitor Cell (MAPC)-like cells towards neural cells cannot depend on morphology and a limited set of neural markers" *Exp. Neurol.* 203(2):542-554 (Feb. 2007) (abstract only).

Rooney, G.E., et al. "Elevation of cAMP in Mesenchymal Stem Cells Transiently Upregulates Neural Markers rather than Inducing Neural Differentiation" Epub ahead of print, *Stem Cells Dev.* (Jun. 13, 2008) (abstract only).

Scintu, F., et al. "Differentiation of human bone marrow stem cells into cells with a neural phenotype: diverse efffects of two specific treatments" *BMC Neuroscience* 7:14 (Feb. 16, 2006).

Suon, S., et al. "Transient Differentiation of Adult Human Bone Marrow Cells into Neuron-like Cells in Culture: Development of Morphological and Biochemical Traits Is Mediated by Different Molecular Mechanisms" *Stem Cells Dev.* 13(6):625-635 (Dec. 2004). Author Manuscript, PMC, Sep. 11, 2007.

* cited by examiner

DIRECTED IN VITRO DIFFERENTIATION OF MARROW STROMAL CELLS INTO NEURAL CELL PROGENITORS

CROSS REFERENCE TO RELATED APPLICATIONS

This application is a divisional of U.S. Ser. No. 10/153,972, filed May 23, 2002 now abandoned, which claims priority under 35 U.S.C. § 119(e) to U.S. Provisional Application No. 60/294,281,filed May 30, 2001, both of which are incorporated herein by reference in their entirety.

STATEMENT REGARDING FEDERALLY SPONSORED RESEARCH OR DEVELOPMENT

The invention was made in part using funds obtained from the U.S. Government (National Institutes of Health Grant Nos. AR47161 and AR42210) and the U.S. government may have certain rights in the invention.

BACKGROUND OF THE INVENTION

Human marrow stromal cells (hMSCs) are multipotential adult stem cells that contribute to the regeneration of tissues such as bone, cartilage, fat, and muscle (1997, Friedenstein, et al., Exp. Hematol. 4(5):267-274; 1997, Prockop, D J, Science, 276(5309):71-74; 1999, Pittenger, et al., Science, 284 (5411):143-147; 1998, Ferrari et al., Science, 279(5356): 1528-1530).

The recent discovery of stem cell populations in the central nervous system (CNS) has generated intense interest, since the brain has long been regarded as incapable of regeneration (Reynolds and Weiss, 1992, Science 255:1707-1710; Richards et al., 1992, Proc. Natl. Acad. Sci. USA 89:8591-8595; Morshead et al., 1994, Neuron 13:1071-1082). Neural stem cells (NSCs) are capable of undergoing expansion and differentiating into neurons, astrocytes and oligodendrocytes in vitro (Reynolds and Weiss, 1992, Science 255:1707-1710; Johansson et al., 1999, Cell 96:25-34; Gage et al., 1995, Annu. Rev. Neurosci. 18:159-192; Vescovi et al., 1993, Neuron 11:951-966). NSCs back transplanted into the adult rodent brain survive and differentiate into neurons and glia, raising the possibility of therapeutic potential (Lundberg et al., 1997, Exp. Neurol. 145:342-360; Lundberg et al., 1996, Brain Res. 737:295-300; Renfranz et al., 1991, Cell 66:713-729; Flax et al., 1998, Nature Biotech. 16:1033-1039; Gage et al., 1995, Proc. Natl. Acad. Sci. USA 92:11879-11883; Svendsen et al., 1997, Exp. Neurol. 148:135-146). However, the inaccessibility of NSC sources deep in the brain severely limits clinical utility. The recent report demonstrating that NSCs can generate hematopoietic cells in vivo suggests that hematopoietic stem cell populations may be less restricted than previously thought (Bjornson, 1999, Science 283:534-537).

Recent data suggest that MSCs can also be induced to differentiate into neural cells in vivo. It has been found that hMSCs integrate and migrate along the known pathway for the migration of neural stem cells after being infused into rat brain (Azizi, et al., 1998, PNAS, 95(7):3908-3913). Other data demonstrate that mouse MSCs (mMSCs) labeled with BrdU migrate to both forebrain and cerebellum without disruption of normal brain structure when injected into the lateral ventricle of a neonatal mouse (Kopen, et al., 1999, PNAS, 96(19):10711-10716). Some of the mMSCs differentiated into cells that had astrocyte morphology and expressed the astrocyte-specific protein glial fibrillary acid protein (GFAP). Further, some of the mMSCs appeared in the olfactory bulb and the internal granular layer of the cerebellum, both of which are neuron-rich regions. Finally, the Kopen study also demonstrated that some BrdU-labeled mMSCs found in the reticular formation of the brain stem were positive for neurofilament.

Other investigations report conditions under which MSCs may be differentiated in culture into neural-like cells. Woodbury et al. demonstrate that cells may be differentiated either by serum withdrawal and exposure to beta-mercaptoethanol (BME), or by treatment of the MSCs with butylated hydroxytoluene (BHT) and dimethylsulfoxide (DMSO) (Woodbury et al., 2000, J. Neurosci. Res., 61(4):364-370). Others report that MSCs may be differentiated into neural-like cells by treatment with epidermal growth factor (EGF) followed by brain derived growth factor (BDGF), or by co-culture with a suspension of rat or mouse midbrain cells (Sanchez-Ramos et al., 2000, Exp. Neurol., 164(2):247-256).

However, until the present invention, a need has existed to elucidate the early steps of neural differentiation so that, cells at different early stages of differentiation may be identical and used in therapy. The present invention fulfills this need.

SUMMARY OF THE INVENTION

The present invention encompasses a method of producing a neural cell. The method comprises increasing the intracellular level of cyclic AMP in an isolated marrow stromal cell, thereby producing a neural cell. In a preferred aspect, the neural cell produced by the method is human.

In another aspect, the method comprises increasing the intracellular level of cyclic AMP by treatment of the marrow stromal cell with isobutylmethylxanthine (IBMX) and dibutyryl cyclic AMP (dbcAMP).

The invention also includes a method of treating a human patient having a disease, disorder, or condition of the central nervous system. The method comprises administering to a patient neural cells produced by the method of increasing intracellular levels of cyclic AMP in an isolated marrow stromal cell.

In a preferred embodiment, the neural cells used to practice this method are transfected with an isolated nucleic acid encoding a therapeutic protein, wherein when the protein is expressed in the neural cells the protein serves to effect treatment of the disease, disorder, or condition. Preferably, the transfected neural cell is human.

In one aspect, the disease, disorder, or condition of the central nervous system is selected from the group consisting of Alzheimer's disease, Parkinson's disease, Huntington's disease, amyotrophic lateral sclerosis, a tumor, a trauma, elderly dementia, Tay-Sach's disease, Sandhoff's disease, Hurler's syndrome, Krabbe's disease, birth-induced traumatic central nervous system injury, epilepsy, multiple sclerosis, trauma, tumor, stroke, and spinal cord injury.

The invention also encompasses a method of treating a human patient in need of neural cells. The method comprises obtaining marrow stromal cells from a human donor, producing neural cells by the increasing intracellular levels of cyclic AMP in the marrow stromal cells, and transplanting the neural cells into the human patient in need of the neural cells, thereby treating the human patient in need of neural cells.

A method of inducing differentiation of an isolated marrow stromal cell into a neural cell comprising contacting the marrow stromal cell with a compound which increases the intracellular levels of cyclic AMP is also contemplated by the invention. Preferably, the compound is a combination of IBMX and dbcAMP, and more preferably, the neural cell so differentiated is human.

A method of treating a patient having a disease, disorder, or condition of the central nervous system is also contemplated by the invention. The method comprises administering to a patient neural cells differentiated by the method of contacting an isolated marrow stromal cell with a compound which increases the intracellular levels of cyclic AMP.

In one aspect, the neural cells so differentiated are transfected with an isolated nucleic acid encoding a therapeutic protein, wherein when the protein is expressed in the neural cells the protein serves to effect treatment of the disease, disorder, or condition. Preferably, the differentiated neural cell is human.

In another aspect, the disease, disorder, or condition of the central nervous system is selected from the group consisting of Alzheimer's disease, Parkinson's disease, Huntington's disease, amyotrophic lateral sclerosis, a tumor, a trauma, elderly dementia, Tay-Sach's disease, Sandhoff's disease, Hurler's syndrome, Krabbe's disease, birth-induced traumatic central nervous system injury, epilepsy, multiple sclerosis, trauma, tumor, stroke, and spinal cord injury.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. However, it should be understood that the invention is not limited to the precise arrangements and instrumentalities shown. In the drawings:

FIGS. 1A-1D, is a quartet of images depicting induction of neural morphology in hMSCs. FIG. 1A is an image depicting untreated hMSCs. FIGS. 1B, 1C, and 1D depict hMSCs treated with 0.5 millimolar isobutylmethylxanthine (IBMX) and 1 millimolar dibutyryl cyclic AMP (dbcAMP) for 6 days. Arrows represent differentiated neuron-like cells while undifferentiated hMSCs are indicated by an arrow head. 200× Magnification.

DETAILED DESCRIPTION OF THE INVENTION

The invention herein described demonstrates another way to differentiate MSCs to cells with many characteristics of early neurons and glia. The method of differentiation involves increasing levels of intracellular cyclic AMP by treating the MSCs with dibutyryl cyclic AMP (dbcAMP) and isobutylmethylxanthine (IBMX).

The invention comprises and utilizes the discovery that increasing cyclic AMP levels in marrow stromal cells mediates differentiation of the cells into neural cells expressing a variety of early-expressed neuron-specific markers (e.g. neuron-specific enolase (NSE), vimentin, MAP1B, and the like). The cells exhibit other neuron-like phenotypic characteristics such as, but not limited to, spherical and retractile cell bodies exhibiting typical neural perikaryal appearance, cell bodies extending long processes terminating in growth cones and filopodia typical of neurons. Thus, the methods disclosed herein induce marrow stromal cell differentiation into immature neural cells. Such methods are crucial in the development of cell-based therapeutics for treatment of central nervous system (CNS) disorders, diseases or conditions. Indeed, prior to the present invention, the lack of clarity with respect to neural differentiation has severely impeded the development of CNS therapeutics.

The invention includes a method of inducing an isolated marrow stromal cell to differentiate into an isolated neural cell. Embodiments of the method of the invention are described in the Examples section herein. Generally, bone marrow cells are isolated from a donor, stromal cells are obtained therefrom, and the stromal cells are subsequently cultured in vitro on culture plates using standard cell culture techniques, e.g., as described in the materials and methods section of the Examples. Preferably, the donor is a human, however, the invention is intended to encompass a mammalian donor and should not be limited to the specific donors disclosed herein.

Figure 1:
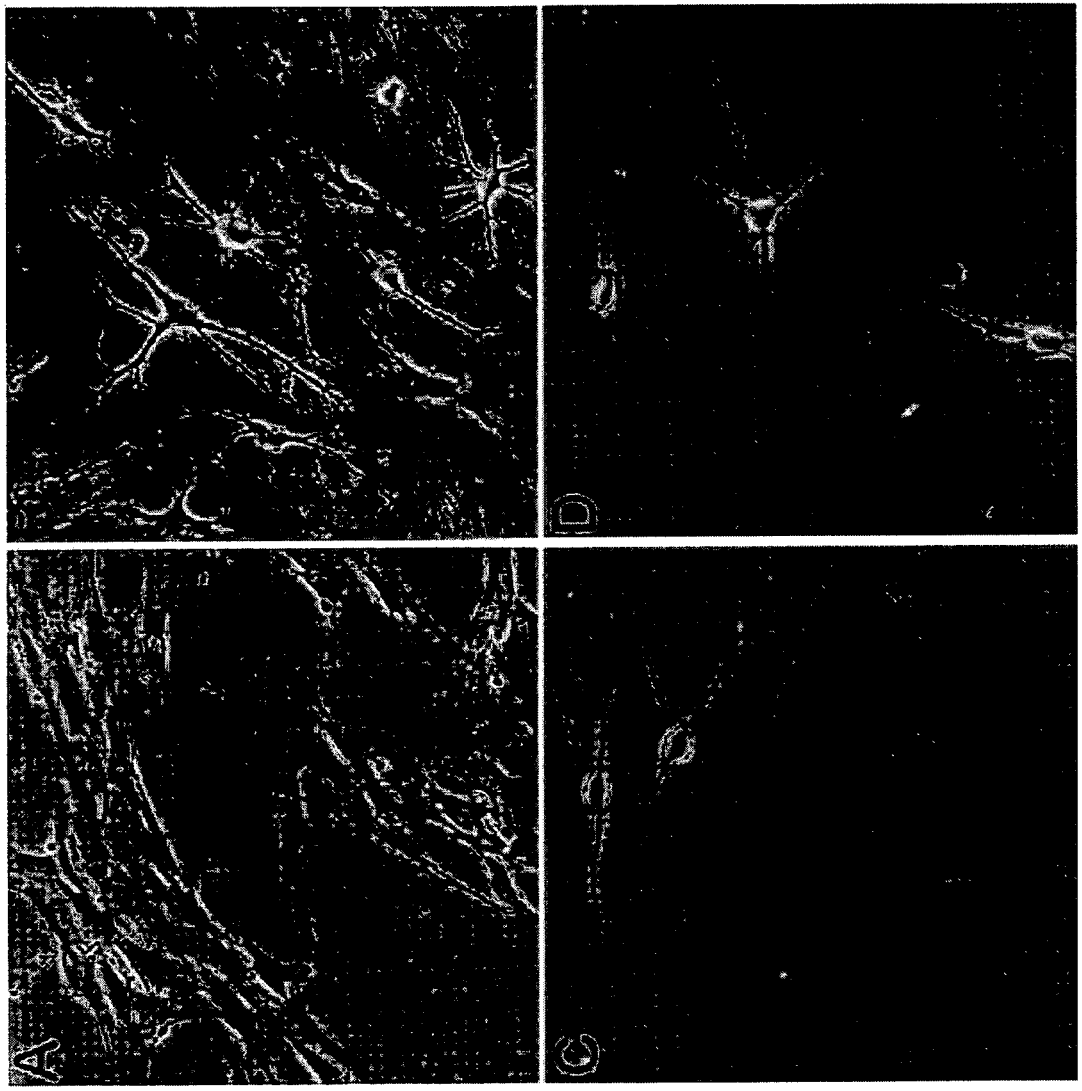
FIG. 1, comprising

To induce the immature neural phenotype, the cells are treated with an effective amount of a compound capable of increasing cyclic AMP levels in marrow stromal cells. This compound is introduced into the cell culture for a period of time. The length of time may vary according to the precise method being contemplated and should not be construed as limiting the invention in any way. After treatment, the cells are prepared for Western blot assay to determine expression patterns of various neural markers. Neural morphology is evident within about two days, see FIG. 1 for example, and the morphology becomes more evident steadily over time.

In one embodiment of the invention, a combination of isobutylmethylxanthine (IBMX) and dibutyryl cyclic AMP (dbcAMP) is used to increase the levels of intracellular cyclic AMP. This particularly preferred embodiment is more fully discussed in the Examples section herein disclosed. However, the invention is not limited to the compounds disclosed herein and should be construed to include all compounds capable of increasing intracellular cyclic AMP levels in a marrow stromal cell. Such compounds include, but are not limited to epinephrine, isoproterenol, and forskolin.

Powder forms of IBMX and dbcAMP, prepared in water, may be administered to isolated marrow stromal cells in culture in combination in a range of 0.01 millimolar to 5.0 millimolar IBMX and 0.1 millimolar to 10.0 millimolar dbcAMP. Preferably, the range is 0.2 millimolar to 1.0 millimolar IBMX and 0.2 millimolar to 2.0 millimolar dbcAMP. Most preferably, a combination of IBMX at a concentration of 0.5 millimolar and dbcAMP at a concentration of 1 millimolar is administered to the isolated marrow stromal cells in culture. The IBMX/dbcAMP solution is preferably prepared in water. It is also preferred that IBMX and dbcAMP be used as a combined solution.

Administration of a cAMP-stimulating compound is preferably delivered to from about thirty cells to about one million cells per fifty-eight square centimeter culture dish. More preferably, the range of cells is from about ten thousand to about one million cells per dish, and most preferable, the cAMP-stimulating compound is administered to about one million cells per fifty-eight square centimeter dish.

Treatment of the cells with a cAMP-stimulating compound can last from 0.5 to 60 days. Preferably, the treatment will extend from 5 to 10 days, and more preferably, the cells are treated for 6 days. The number of days of treatment of the marrow stromal cells with a cAMP-stimulating compound is dependent upon the development of neural morphology.

Neural identity can be confirmed by Western blot assay for detection of early neural markers. Examples of such early markers are neuron-specific enolase (NSE), MAP1B, and TuJ. Progressive differentiation of the marrow stromal cell to the neural cell corresponds with an increase in each of these markers, indicating that neural cells are produced. Other procedures may also be employed to determine neural identity.

It is apparent from the data disclosed herein that it is possible to differentiate isolated marrow stromal cell into neural cells in vitro. Neural cells so differentiated are useful in treating patients afflicted with any of a wide variety of central nervous system diseases, disorders, or conditions.

The invention also includes a method for producing an isolated neural cell from isolated marrow stromal cells. The method comprises differentiating an isolated marrow stromal cell in the same general manner as recited above, thereby producing an isolated neural cell.

The isolated neural cell recited in both of the methods above may be transfected with an isolated nucleic acid encoding a therapeutic protein. The therapeutic protein, when expressed, will treat a patient having a disease, disorder, or condition of the central nervous system.

A wide plethora of therapeutic proteins are well known in the art and are set forth in, for example, WO 96/30031 and WO 99/43286. Such examples include, but are not limited to, cytokines, chemokines, neurotrophins, other trophic proteins, growth factors, antibodies, and glioma toxic protein. When the transfected neural cells encoding such proteins are administered to a patient, the neural cells will therapeutically influence cells, which are already present in the central nervous system. For example, transfected neural cells which are introduced into the central nervous system may be used to repair any central nervous system damage, and/or to combat tumors of the central nervous system.

International patent applications WO 96/30031 and WO 99/43286 also describe use of MSCs in therapies for a wide variety of CNS diseases, disorders, or conditions, which include, but are not limited to, genetic diseases of the CNS (e.g., Tay-Sach's, Sandhoffs disease, Hurler's syndrome, Krabbe's disease), birth-induced traumatic CNS injury, adult CNS diseases, disorders or conditions (e.g., Parkinson's, Alzheimer's, and Huntington's diseases, elderly dementia, epilepsy, amyotropic lateral sclerosis, multiple sclerosis, trauma, tumors, stroke, and the like) and degenerative diseases and traumatic injury of the spinal cord.

Among neonates and children, transfected neural cells may be used for treatment of a number of genetic diseases of the central nervous system, including, but not limited to, Tay-Sachs disease and the related Sandhoffs disease, Hurler's syndrome and related mucopolysaccharidoses and Krabbe's disease. To varying extents, these diseases also produce lesions in the spinal cord and peripheral nerves and they also have non-neurological effects. While the non-neurological effects of these diseases may be treatable by bone marrow transplantation, the central nervous system effects do not improve despite bone marrow transplantation. The method of the present invention is useful to address the central nervous system effects of these types of diseases. In addition, in neonates and children, head trauma during birth or following birth is treatable by introducing these neural cells directly into the central nervous system of the children. Central nervous system tumor formation in children is also treatable using the methods of the present invention.

Adult diseases of the central nervous system are also treatable by administering isolated neural cells to the adult. Such adult diseases include but are not limited to, Parkinson's disease, Alzheimer's disease, spinal cord injury, stroke, trauma, tumors, degenerative diseases of the spinal cord such as amyotropic lateral sclerosis, Huntington's disease and epilepsy. Treatment of multiple sclerosis is also contemplated.

Treatment of spinal cord injuries is also possible using the method of the present invention. Prior art methods of treating spinal cord injuries involve using fibroblast cells to deliver neurotrophins to the site of spinal cord lesions in animals. The neurotrophins, delivered in this manner, reduce the lesion or otherwise treat the injury. However, fibroblasts produce large amounts of collagen, causing fibrosis at the site of the lesion, thus negating the therapeutic effects of the treatment. Delivery of neurotrophins to spinal cord lesions using transfected neural cells is advantageous over prior art methods because neural cells do not produce large amounts of collagen and therefore should not cause fibrosis.

The isolated neural cell recited in both of the methods above may also be transfected with an isolated nucleic acid encoding a regulatory protein. The regulatory protein, when expressed, will regulate the expression of a protein involved in a disease, disorder, or condition of the central nervous system, thereby controlling the disease state. The regulatory protein may be, for example, neural growth factor, brain derived growth factor, epidermal growth factor, fibroblast growth factor, glial derived growth factor, and stem cell factor.

The invention further includes a method of treating a human patient having a disease, disorder, or condition of the central nervous system by administering the differentiated neural cells of the invention to the central nervous system of the patient. Methods of treating a human patient using MSCs are described in WO 96/30031 and WO 99/43286, which are incorporated by reference as if set forth in their entirety herein. Methods of administering differentiated neural cells to a patient are identical to those used for MSCs as described in WO 96/30031 and WO 99/43286. The methods encompass introduction of an isolated nucleic acid encoding a therapeutic protein into differentiated neural cells and also encompassing differentiated neural cells themselves in cell-based therapeutics where a patient is in need of the administration of such cells. The differentiated neural cells are preferably administered to a human, and further, the neural cells are preferably administered to the central nervous system of the human. In some instances, the differentiated neural cells are administered to the corpus striatum portion of the human brain. The precise site of administration of the neural cells will depend on any number of factors, including but not limited to, the site of the lesion to be treated, the type of disease being treated, the age of the human and the severity of the disease, and the like. Determination of the site of administration is well within the skill of the artisan versed in the administration of cells to mammals.

The mode of administration of the differentiated neural cells to the central nervous system of the human may vary depending on several factors including but not limited to, the type of disease being treated, the age of the human, whether the neural cells have isolated DNA introduced therein, and the like. Generally, cells are introduced into the brain of a mammal by first creating a hole in the cranium through which the cells are passed into the brain tissue. Cells may be introduced by direct injection, by using a shunt, or by any other means used in the art for the introduction of compounds into the central nervous system. Intravenous administration may also be used to introduce the cells into a patient.

Definitions

The articles "a" and "an" are used herein to refer to one or to more than one (i.e. to at least one) of the grammatical object of the article. By way of example, "an element" means one element or more than one element.

As used herein, "central nervous system" should be construed to include brain and/or the spinal cord of a mammal. The term may also include the eye and optic nerve in some instances.

As used herein, "stromal cells", "isolated marrow stromal cells", and "MSCs" are used interchangeably and are meant to refer to the small fraction of cells in bone marrow which can serve as stem cell-like precursors of osteocytes, chondrocytes, monocytes, and adipocytes and which are isolated from bone marrow by their ability adhere to plastic dishes. Marrow stromal cells may be derived from any animal. In some embodiments, stromal cells are derived from primates, preferably humans.

As used herein, the term "therapeutic protein" is meant to refer to a protein which can compensate for the protein encoded by a defective gene and/or insufficient gene expression that is causally linked to the disease or symptoms of the disease, disorder or condition characterized by a gene defect. The presence of the protein alleviates, reduces, prevents, or causes to be alleviated, reduced or prevented, the causes and/or symptoms that characterize the disease, disorder, or condition. A therapeutic protein is also meant to refer to a protein which down-regulates a hyperexpressed gene, upregulates a hypoexpressed gene, speeds a repair process, increases replication or differentiation of exogenous or endogenous stem cells, or causes synthesis of a compound or compounds that improve the function or survival of neural cells.

As used herein, a "disease, disorder or condition" which can be treated with a therapeutic protein is meant to refer to a disease, disorder or condition that can be treated or prevented by the presence of a protein which alleviates, reduces, prevents or causes to be alleviated, reduced or prevented, the causes and/or symptoms that characterize the disease, disorder or condition. Diseases, disorders and conditions which can be treated with a therapeutic protein include diseases, disorders and conditions characterized by a gene defect as well as those which are not characterized by a gene defect but which nonetheless can be treated or prevented by the presence of a protein which alleviates, reduces, prevents or causes to be alleviated, reduced or prevented, the causes and/or symptoms that characterize the disease, disorder or condition.

The term "isolated nucleic acid" should be construed to refer to a nucleic acid sequence, or segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

As used herein, "transfected cells" is meant to refer to cells to which a gene construct has been provided using any technology used to introduce nucleic acid molecules into cells such as, but not limited to, classical transfection (calcium phosphate or DEAE dextran mediated transfection), electroporation, microinjection, liposome-mediated transfer, chemical-mediated transfer, ligand mediated transfer or recombinant viral vector transfer.

The term "differentiation" as used herein, should be construed to mean the induction of a differentiated phenotype in an undifferentiated cell by coculturing the undifferentiated cell in the presence of a substantially homogeneous population of differentiated cells, in the presence of products of differentiated cells or in the presence of an inducer of cell differentiation.

The term "neural cell" as used herein should be construed to mean an MSC differentiated such that it expresses at least one of the following neural markers: neuron-specific enolase (NSE), TuJ, vimentin, and MAP The term "neuron" as used herein should be construed to mean a nerve cell capable of receiving and conducting electrical impulses from the central nervous system. A nerve cell or "neuron" typically comprises a cell body, an axon, axon terminals, and dendrites.

As used herein, the term "cAMP-stimulating compound" is meant to refer to those compounds which increase intracellular cyclic AMP levels in a cell. Examples of such cAMP-stimulating compounds include, but are not limited to epinephrine, isoproterenol, forskolin, IBMX and dbcAMP.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods are now discussed.

Isolation and Culture of hMSCs

Twenty milliliters of bone marrow aspirate were taken from the iliac crest of normal donors ranging in age from 19 to 49 years old. Isolation and culture of hMSCs were carried out as previously described by DiGirolamo et al. (1999, Br. J. Haematol., 107(2):275-281). Briefly, aspirate was diluted 1:1 with Hanks' balanced salt solution (HBSS; Gibco-BRL, St. Louis, Mo.) and layered over 10 milliliters of Ficoll (Ficoll-Paque; Pharmacia). After centrifugation at 2,500 g for 30 minutes, the mononuclear cell layer was recovered from the gradient interface and washed with HBSS. The mononuclear cells were centrifuged at 1,500 g for 15 minutes and resuspended in complete culture medium (alpha-MEM; Gibco-BRL) containing 20% fetal bovine serum (FBS; lot-selected for rapid growth of hMSCs, Atlanta Biologicals), 100 units per milliliter of penicillin, 100 micrograms per milliliter of streptomycin; and 2 millimolar L-glutamine (Gibco-BRL). All of the cells were plated in 25 milliliters of medium in a 150 centimeters squared culture dish (Falcon) and incubated at 37 degrees Celsius with 5 percent humidified carbon dioxide. After 24 hours, non-adherent cells were discarded, and adherent cells were thoroughly washed twice with phosphate-buffered saline (PBS). Fresh complete culture medium was added or replaced every 3 or 4 days. The cells were grown to approximately 70 to 90 percent confluency over about 14 days. The cells (from passage 0) were harvested with 0.25 percent trypsin and 1 millimolar EDTA for 5 minutes at 37 degrees Celsius, replated in 75 centimeters squared flasks (Falcon) at 5,000 cells per centimeter squared, and again grown to near confluency. The cells (from passage 1) were harvested with the same concentrations of trypsin and EDTA, suspended at approximately one million to two million cells per milliliter in 5 percent DMSO and 30 percent FBS, and frozen as one milliliter aliquots in liquid nitrogen. To expand a culture, a frozen stock of hMSCs was thawed, plated at 5,000 cells per centimeter squared, and grown to approximately 70 to 90 percent confluency over about 3 to 7 days. The cells (from passage 2) were harvested with the same concentrations of trypsin and EDTA and diluted 1:3 per passage for further expansion.

Neural Differentiation Protocol

Powder forms of Isobutylmethylxanthine (IBMX) were dissolution Dimethyl Sulfoxide (DMSO). Powder forms of Dibutyryl Cyclic AMP (dbcAMP) were dissolved in $dH_2O$. A final concentration of 0.5 millimolar IBMX (Sigma)/1 millimolar dbcAMP (Sigma) was achieved and this solution was added to 10 milliliters of complete culture medium containing one million hMSCs (passage 2) in a fifty-eight square centimeter tissue culture dish (Falcon). IBMX/dbcAMP and complete culture medium were replaced at three days and the incubation continued through six days.

Western Blot Analysis

Cells were rinsed with cold phosphate buffered saline (PBS) twice and drained. Whole cell lysates were prepared by adding 0.5 milliliters of detergent-based cell lysis buffer (1 percent (w/w) NP-40, 0.5 percent (w/v) sodium deoxycholate, 0.1 percent (w/v) sodium dodecylsulfate (SDS), prepared in PBS) plus leupeptin (final concentration at 0.1 milligrams per milliliter, freshly prepared and added; Sigma), and scraping the cells into a centrifuge tube. The cells were further lysed by flushing them 3 times through a 1 milliliter capacity syringe with a 21 gauge needle, and then phenylmethylsulfonyl fluoride (PMSF; final concentration of 574 micromolar prepared in isopropanol, Sigma) was added to the cell suspension. The sample was incubated on ice for 45 minutes, centrifuged at 15,000 g for 30 minutes at 4 degrees Celsius, and the supernatant was collected. Protein content was assayed colorimetrically (Micro Protein Kit, Sigma). Five micrograms of the cell lysate were loaded onto a 4 to 10 percent or 4 to 20 percent polyacrylamide gradient gel. After electrophoresis, the protein was transferred by electroelution onto a nitrocellulose membrane. Immunodetection of each of the neuron markers shown in Table 1 was performed with the following primary antibodies: rabbit anti-NSE (ICN Biomedicals, 1:10,000 dilution), mouse anti-vimentin (DAKO, 1:1,000 dilution), rabbit anti-MAP1B (1:10,000 dilution; 1994, Black et al., J. Neurosci. 14:857-870), mouse anti-TuJ-1 (BabCo, 1:2,000 dilution), mouse anti-alpha-tubulin (Sigma, 1:4,000 dilution), rabbit anti-neurofilament M (NF-M, Chemicon International, Inc., 1:1,000 dilution), mouse anti-MAP2 (2a+2b, Pharmingen, 1:1,000 dilution), mouse anti-tau (Tau-2, Pharmingen, 1:500 dilution), mouse anti-S-100 (Neomarkers, 1:500 dilution), mouse anti-human GFAP (DAKO, 1:500 dilution), and mouse anti-myelin basic protein (MBP, Chemicon International, 1:1,000 dilution).

The secondary antibody was horseradish peroxidase conjugated to either goat anti-rabbit IgG or anti-mouse IgG. The membranes were processed using enhanced chemiluminescence (ECL Western blotting detection reagents, Amersham Pharmacia Biotech). About 0.5 micrograms of human brain extract (Clontech) was used as a control.

The results of the experimental examples are now discussed.

Figure 2:
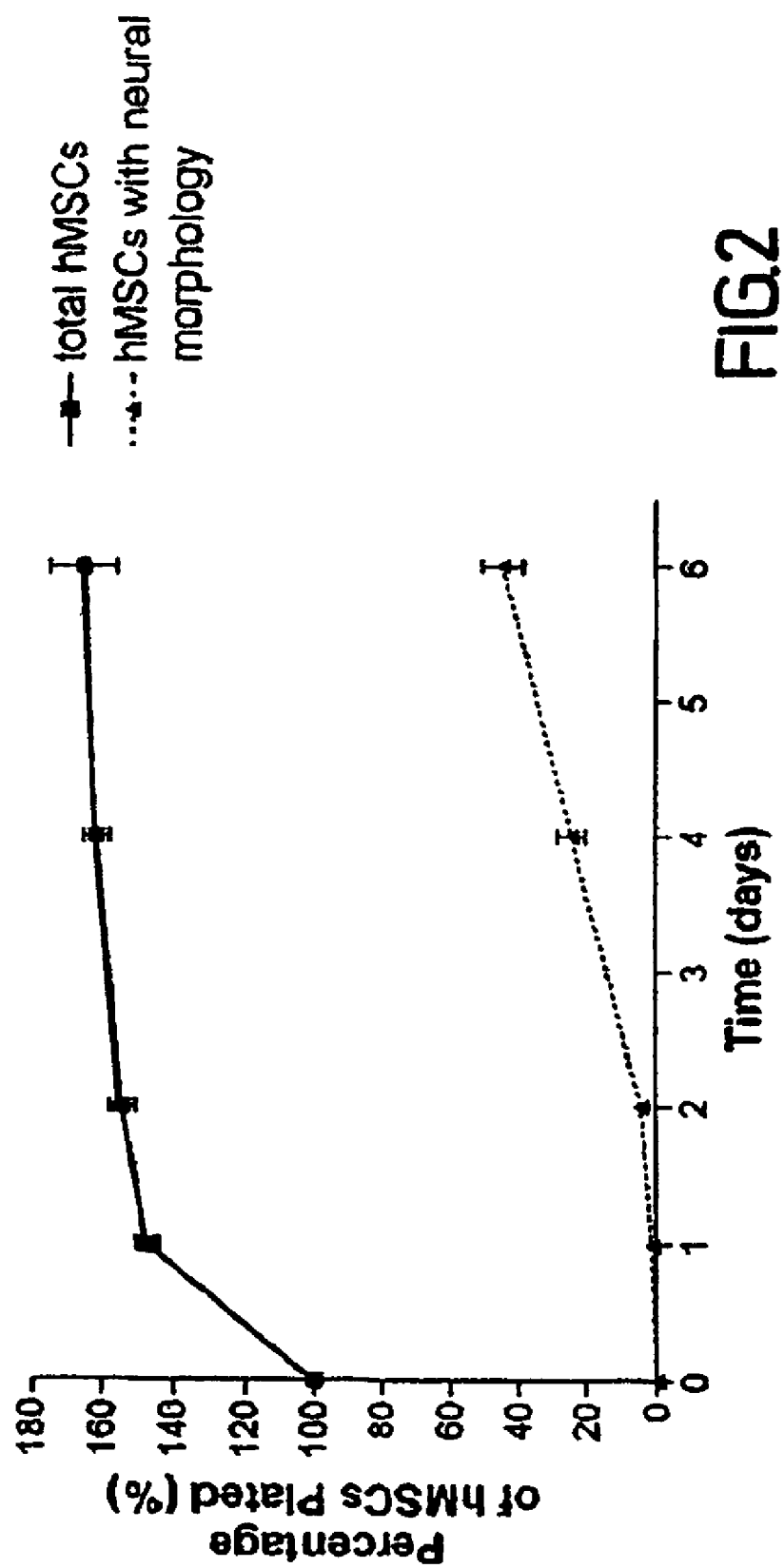
FIG. 2 is a graph representing cellular proliferation and neural differentiation in hMSCs treated with 0.5 millimolar IBMX and 1 millimolar dbcAMP. The data points represent mean ± standard deviation of results of experiments performed in triplicate. Cells were scored as hMSCs with neural morphology by the presence of a refractile cell body, multipolar processes, and growth-cone-like structures.

Induction of Neural Morphology on hMSCs hMSCs (FIG. 1A) were induced to differentiate in culture by incubation with 0.5 millimolar IBMX/1 millimolar dbcAMP. Typical neural cells were identified as early as two days later (FIGS. 1B, 1C, and 1D). After 6 days, neural cells accounted for about 25% of the total population (FIG. 2). The cells had morphological features typical of neurons such as refractile cell bodies and long branching processes with growth cone-like terminal structures that frequently made contact with undifferentiated hMSCs. There was a reduced rate of cellular proliferation, but there was no obvious evidence of cell death. However, after IBMX/dbcAMP was withdrawn from the complete culture medium of the hMSCs that were treated for 6 days, all neural cells died within several days. The remaining cells stopped dividing and showed senescence morphology. The data suggested that the differentiation was not reversible.

Biochemical Analysis of Cell Phenotype

Figure 3:
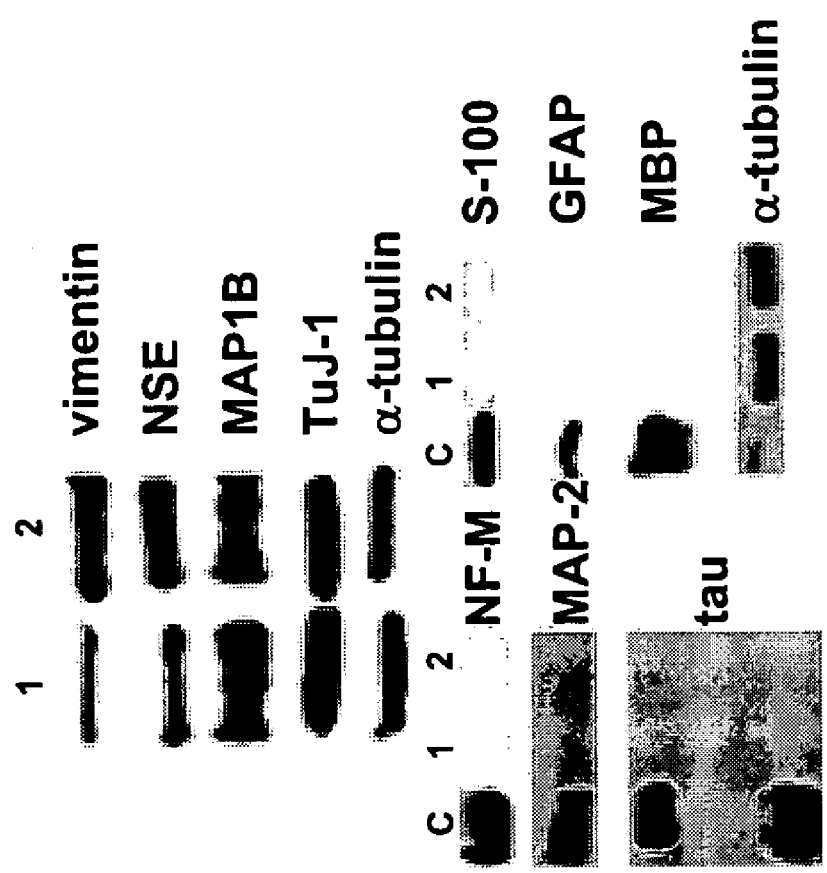
FIG. 3 is an image depicting a Western blot assay of expression of vimentin, neuron-specific enolase (NSE), MAP1B, TuJ, NF-M, MAP-2, tau, S-100, GFAP, MBP, and alpha-tubulin in treated and untreated hMSCs. Lane C shows expression of the listed neural markers in control, human brain extract. Lane 1 shows expression in untreated hMSCs, and Lane 2 shows expression in hMSCs treated with 0.5 millimolar IBMX and 1 millimolar dbcAMP for 6 days.

Using the Western blot assay, it was determined that the untreated hMSCs expressed several markers characteristic of neural cells such as MAPNB, NSE, TuJ-1 and vimentin (FIG. 3). Using alpha-tubulin as a control, it was demonstrated that the expression levels of both NSE and vimentin were increased after incubation with 0.5 millimolar IBMX and 1 millimolar dbcAMP. The increase in NSE and vimentin mRNAs coincided with the appearance of neural cells in the cultures. However, there was no change in the expression level of either MAP1B or TuJ-1 (FIG. 3). Since NSE, MAP1B, and TuJ-1 are early neuron-characteristic markers, and vimentin is an early marker for glia, the data suggested that hMSCs differentiated in vitro into some early progenitors of either neurons or glia. Expression of NF-M, MAP2, tau, S-100, GFAP, and MBP, all markers of mature neurons (FIG. 3), was not detected in either untreated or IBMX/dbcAMP-treated hMSCs.

IBMX is a phosphodiesterase inhibitor and dbcAMP is a cAMP analogue. Both agents are known to elevate intracellular cAMP levels. Moore et al. (1996, Mol.& Chem. Neuropathol. 29(2-3):107-126) found that IBMX or dbcAMP can greatly increase the extension of processes in a medulloblastoma cell line, MCD-1. The formation of long processes induced by IBMX was associated with a decrease in cell proliferation as evidenced by a reduction in numbers of cells incorporating 5-bromo-2-deoxyuridine (BrdU). Bang et al. (1994, PNAS, 91(12):5330-5334) found that elevation of cAMP through addition of dbcAMP and IBMX induced a neuronal morphology in human prostate carcinoma cells. The changes also included increased expression of NSE, terminal differentiation, $G_1$ synchronization, growth arrest, and loss of clonogenicity. Cox et al. (1999, Cancer Res., 59(15):3821-3830) also found agents that can elevate intracellular cAMP such as epinephrine, isoproterenol, forskolin, IBMX, and dbcAMP can induce prostate tumor cells to assume many of the characteristics of neuroendocrine cells. The cells reverted to their original phenotype when the agents were removed. With C6 glioma cells, both Sharma et al. (1987, J. Neurosci. Res., 17(2):135-141) and Ghosh et al. (1997, Cell Biol. Int., 21(9):551-557) found that dbcAMP induced neural differentiation.

In the experiments presented here, MSCs were cultured under conditions that increase intracellular cAMP, and it was determined that a fraction of the cells in the cultures developed some of the phenotypic features of neural cells. The results were similar but not identical to the observations recently reported by Woodbury et al. and Sanchez-Ramos et al. using different culture conditions (Table 1). Similar morphological changes were seen with all three experimental conditions, but the number of neural-like cells varied widely. Our results were similar to those of Woodbury et al. in that we saw an increased expression of NSE, but no expression of GFAP. In contrast, Sanchez-Ramos et al. observed expression of GFAP both before and after differentiation under their conditions. Expression of either NF-M or tau that Woodbury et al. observed after differentiation was not detected. Under the present conditions, there was increased expression of vimentin, as is seen in differentiation of glia. MAP1B and TuJ-1, two markers for early neurons, were expressed at about the same levels before and after differentiation. MAP-2, a marker for mature neurons, was negative. S-100 and MBP, markers for mature astrocytes and oligodendroglia, were also negative. Therefore, the results suggest that the cells differentiated into early neural progenitors under conditions that increase intracellular cAMP but not into mature cells of any specific lineage. Differentiation of the cells into mature neural cells will probably require a combination of the conditions tested to date and fiuctional assays such as the membrane potentials of putative neurons.

TABLE 1

| | WOODBURY | | SANCHEZ-RAMOS Conditions | | INVENTION | |
|---|---|---|---|---|---|---|
| | BME or DMSO/BHA | | EGF/BDNF and RA or co-culture Species | | DbcAMP and IBMX | |
| | Rat/Human | | Mouse/Human Percent Cells with Neural Morphology | | Human | |
| | Greater than 50 | | 0.2 to 5 | | 25 | |
| | Cytochem | Western | Cytochem | Western | Cytochem | Western |
| NSE | +/+++ | +/+++ | | | | +/+++ |
| NF-M | 0/+++ | | | | | 0/0 |
| Tau | 0/+++ | | | | | 0/0 |
| Neu-N | 0/++ | | +/++ | ++/++ | | |
| Nestin | 0/+ to 0 | | /++ | ++/0 | | |
| GFAP | 0/0 | | /++ | ++/++ | | 0/0 |
| TrkA | 0/+++ | | | | | |
| Vimentin | | | | | | +/+++ |
| MAP1B | | | | | | ++/++ |
| TuJ-1 | | | | | | ++/++ |
| MAP-2 | | | 0/0 | | | 0/0 |
| S-100 | | | | | | 0/0 |
| MBP | | | | | | 0/0 |
| Fibronectin | | | +++/+ | | | |

Comparisons of observations on differentiation of MSCs. Observations are presented as 0 to +++ scores before/after differentiation. The scores are approximations based on data presented in different formats by Woodbury et al. and Sanchez-Ramos et al. Parallel assays by immunocytochemistry (Cytochem) and Western blots were not performed in many of the experiments.

The morphological changes of the hMSCs coincide with an increase in NSE and vimentin expression. However, several markers for mature neurons and glia are not expressed, indicating that the present invention may be useful in studying the early steps of neural cell differentiation. The results also indicate that these early progenitor neural cells have a potential therapeutic use in treating diseases, conditions and disorders of the central nervous system.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

We claim:

1. A method of producing a neural progenitor cell, said method comprising contacting an isolated bone marrow stromal cell with a compound that induces differentiation of said bone marrow stromal cell, wherein the compound is a cyclic AMP-stimulating compound that increases the intracellular level of cyclic AMP in said bone marrow stromal cell, thereby producing a neural progenitor cell.

2. The method of claim 1, wherein said cyclic AMP-stimulating compound is selected from the group consisting of epinephrine, isoproterenol, forskolin, isobutylmethylxanthine (IBMX), dibutyryl cyclic AMP (dbcAMP), and a combination of IBMX and dbcAMP.

3. The method of claim 2, wherein said cyclic AMP-stimulating compound is a combination of IBMX and dbcAMP.

4. The method of claim 3, wherein said IBMX is present in a concentration of from about 0.01 millimolar to about 5.0 millimolar, and wherein said dbcAMP is present in a concentration of from about 0.1 millimolarto about 10.0 millimolar.

5. The method of claim 4, wherein said IBMX is present at 0.5 millimolar and further wherein said dbcAMP is present at 1 millimolar.

6. The method of claim 1, wherein said bone marrow stromal cell is human.

7. A method of inducing differentiation of an isolated bone marrow stromal cell into a neural progenitor cell, said method comprising contacting said bone marrow stromal cell with a compound that induces differentiation, wherein the compound is a cyclic AMP stimulating compound and results in a neural progenitor cell expressing least one of neuron-specific enolase, TuJ, vimentin or MAP1B.

8. The method of claim 7, wherein said compound is selected from the group consisting of epinephrine, isoproterenol, forskolin, IBMX, dbcAMP, and a combination of IBMX and dbcAMP.

9. The method of claim 8, wherein said compound is a combination of IBMX and dbcAMP.

10. The method of claim 9, wherein said IBMX is present in a concentration of from about 0.01 millimolar to about 5.0 millimolar and wherein said dbcAMP is present in a concentration of from about 0.01 millimolar to about 10.0 millimolar.

11. The method of claim 10, wherein said IBMX is present at a concentration of 0.5 millimolar and wherein said dbcAMP is present at a concentration of 1 millimolar.

12. The method of claim 7, wherein said bone marrow stromal cell is human.

13. A method of producing a neural cell, said method comprising contacting an isolated bone marrow stromal cell with a compound that induces differentiation of said bone marrow stromal cell, wherein the compound is a cyclic AMP-stimulating compound that increases, the intracellular level of cyclic AMP in said bone marrow stromal cell, thereby producing a neural cell and results in a neural cell expressing at neuron-specific enolase, TuJ, vimentin and MAP1B.

14. The method of claim 13, wherein said cyclic AMP-stimulating compound is selected from the group consisting of epinephrine, isoproterenol, forskolin, isobutylmethylxanthine (IBMX), dibutyryl cyclic AMP (dbcAMP), and a combination of IBMX and dbcAMP.

15. The method of claim 14, wherein said cyclic AMP-stimulating compound is a combination of IBMX and dbcAMP.

16. The method of claim 15, wherein said IBMX is present in a concentration of from about 0.01 millimolar to about 5.0 millimolar, and wherein said dbcAMP is present in a concentration of from about 0.1 millimolarto about 10.0 millimolar.

17. The method of claim 16, wherein said IBMX is present at 0.5 millimolar and further wherein said dbcAMP is present at 1 millimolar.

18. The method progenitor neural cell of claim 13, wherein said bone marrow stromal cell is human.

* * * * *